US007844089B2

(12) United States Patent
Kanada et al.

(10) Patent No.: US 7,844,089 B2
(45) Date of Patent: Nov. 30, 2010

(54) IMAGE INTERPRETATION REPORT CREATING APPARATUS

(75) Inventors: Shouji Kanada, Minato-ku (JP); Takahiro Ito, Minato-ku (JP); Yoshifumi Shioe, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 852 days.

(21) Appl. No.: 11/756,339

(22) Filed: May 31, 2007

(65) Prior Publication Data

US 2008/0031503 A1 Feb. 7, 2008

(30) Foreign Application Priority Data

Jun. 2, 2006 (JP) ............................. 2006-155196

(51) Int. Cl.
*G06K 9/00* (2006.01)
*A61B 5/00* (2006.01)

(52) U.S. Cl. .......................................... 382/128; 705/3

(58) Field of Classification Search ................ 382/128, 382/129, 130, 131, 132, 133, 134; 378/4, 378/8, 21–27, 101, 901; 128/920, 922; 705/3; 710/67

See application file for complete search history.

(56) References Cited

U.S. PATENT DOCUMENTS 6,603,494 B1 * 8/2003 Banks et al. ................. 715/807
7,450,742 B2 * 11/2008 Shimizu et al. .............. 382/128

FOREIGN PATENT DOCUMENTS

JP 2003-325458 A 11/2003

* cited by examiner

*Primary Examiner*—Abolfazl Tabatabai
(74) *Attorney, Agent, or Firm*—Sughrue Mion, PLLC

(57) ABSTRACT

An image interpretation report creating apparatus for displaying a case in combination of an image interpretation report and a blood test result even if they are stored in different computers. The apparatus includes: a display unit for displaying an image interpretation report creation screen along with a blood test result; an input unit for specifying finding and a blood test result; a search key generating unit for generating search keys for searching an image interpretation report DB and a blood test result DB; a search processing unit for causing an image interpretation report server and an examination result server to obtain cases that match the search keys; a similarity degree determining unit for displaying the cases in an order of the degree of similarity; and an image interpretation report preservation unit for causing the image interpretation report server to store image interpretation report data.

7 Claims, 24 Drawing Sheets

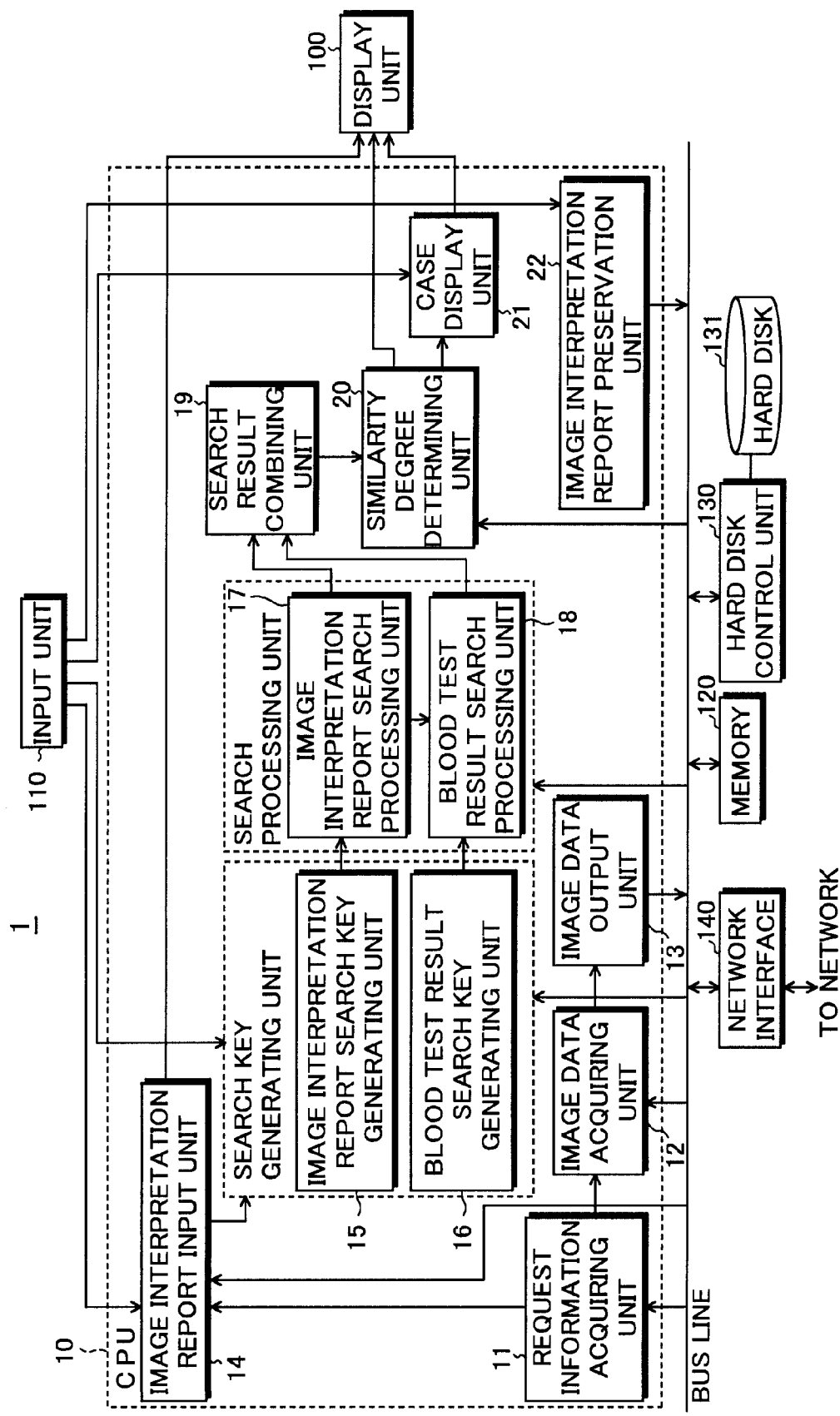

| KEYWORD IN FINDING | SEARCH RANGE |
|---|---|
| PHYMA IN LIVER | ±1 cm AS TO DIAMETER |
| PHYMA IN KIDNEY | ±1.5 cm AS TO DIAMETER |
| ⋮ | ⋮ |

(b)

| SELECTED TEST ITEM | SEARCH RANGE |
|---|---|
| TUMOR MARKER A | ±0.01 mg/liter |
| TUMOR MARKER B | ±0.02 mg/liter |
| ⋮ | ⋮ |

(c)

| RELATION CONDITION BETWEEN IMAGE INTERPRETATION REPORT AND BLOOD TEST |
|---|
| INTERVAL BETWEEN THE DAY OF IMAGING AND THE DAY OF BLOOD SAMPLE COLLECTION IS NOT MORE THAN SEVEN DAYS |
| ⋮ |

FIG.6

EXAMINATION NUMBER: 123456    EXAMINATION KIND: CT    REGION: ABDOMEN
PATIENT NAME: Fuji Taro    SEX: MALE    AGE: 51
DAY OF IMAGING: APRIL 1, 2006
COMMENT: OOOO

— 31

FINDING:

— 32

DIAGNOSIS:

EXAMINATION NUMBER: 123456  EXAMINATION KIND: CT  REGION: ABDOMEN
PATIENT NAME: Fuji Taro  SEX: MALE  AGE: 51
DAY OF IMAGING: APRIL 1, 2006
COMMENT: ○○○ ~31

FINDING: ~32
AFTER OPERATION OF CANCER OF LARGE INTESTINE.
IN SIMPLE CT, MULTIPLE, LOW ABSORBENT PHYMA HAVING A DIAMETER OF 3 CM IS OBSERVED IN LIVER.
IN CONTRAST CT, RING-SHAPED CONTRAST EFFECT IS OBSERVED ON THE PERIPHERY. IT CAN BE THOUGHT TO BE LIVER METASTASIS.
GALLBLADDER, PANCREAS, SPLEEN, AND KIDNEYS ARE NORMAL.
LYMPHADENOPATHY IS RECOGNIZED.

DIAGNOSIS: ~33

FIG.11

| TEST ITEM | TEST RESULT VALUE |
|---|---|
| TUMOR MARKER A | 0.15 mg/liter |
| TUMOR MARKER B | 0.38 mg/liter |
| ... | ... |

BLOOD TEST RESULT
DAY OF BLOOD SAMPLE COLLECTION : MARCH 31, 2006

| SIMILARITY RANKING | PATIENT NAME | SEX | AGE | ... |
|---|---|---|---|---|
| 1 | Shashin Ichiro | MALE | 51 | ... |
| 2 | Suzuki Jiro | MALE | 50 | ... |
| 3 | Tanaka Hanako | FEMALE | 51 | ... |
| 4 | Sato Shiro | MALE | 53 | ... |
| ... | ... | ... | ... | ... |

51 — EXAMINATION NUMBER: 103456  EXAMINATION KIND: CT  REGION: ABDOMEN
PATIENT NAME: Shashin Ichiro  SEX: MALE  AGE: 51
DAY OF IMAGING: AUGUST 1, 2005
COMMENT: OOOO

52 — FINDING:
AFTER OPERATION OF CANCER OF LARGE INTESTINE.
IN SIMPLE CT, LOW ABSORBENT PHYMA HAVING A DIAMETER OF 4 CM.
IN CONTRAST CT, VIVID CONTRAST EFFECT ON THE PERIPHERY.
IT IS DETERMINED TO BE LIVER CANCER. REEXAMINATION IS NECESSARY.
PHYMA IS OBSERVED IN PANCREAS. LYMPHADENOPATHY IS RECOGNIZED.
SPLEEN AND KIDNEYS ARE NORMAL.

53 — DIAGNOSIS:
METASTATIC LIVER CANCER

FIG.16

BLOOD TEST RESULT
DAY OF BLOOD SAMPLE
COLLECTION: JULY 30, 2005

| TEST ITEM | TEST RESULT VALUE |
|---|---|
| TUMOR MARKER A | 0.16 mg/liter |
| TUMOR MARKER B | 0.37 mg/liter |
| ... | ... |

BLOOD TEST RESULT DATA OF "Fuji Taro"
IS NOT ACCUMULATED.
INPUT TEST ITEM AND TEST RESULT
VALUE TO MAKE SEARCH.

35

| TEST ITEM | TEST RESULT VALUE |
|---|---|
|  |  |
| ... | ... |

FIG.22

BLOOD TEST RESULT DATA OF "Fuji Taro" IS NOT ACCUMULATED.
INPUT TEST ITEM AND TEST RESULT VALUE TO MAKE SEARCH.

| TEST ITEM | TEST RESULT VALUE |
|---|---|
| TUMOR MARKER A | 0.15 mg/liter |
| ... | ... |

35

IMAGE INTERPRETATION REPORT CREATING APPARATUS

BACKGROUND OF THE INVENTION

1. Field of the Invention

The present invention relates to an image interpretation report creating apparatus to be used to create an image interpretation report in an image interpretation support system for supporting image interpretation made by a doctor after an examination image (medical image) is photographed which is used for a medical diagnosis by the image.

2. Description of a Related Art

In recent years, accompanying the spread of a medical digital image generation technique such as CR (computed radiography), MRI (magnetic resonance imaging), CT (computed tomography), etc., medical images acquired by examinations are managed electronically.

In general, when an imaging examination is made, before a specific diagnosis of a patient is made by a doctor in charge, an image interpretation of a generated medical image is made by an image interpretation doctor to create an image interpretation report in which an image interpretation result and finding are entered. Conventionally, even when digital image data is generated, a hard copy of a medical image on a photo film is used for image interpretation, however, accompanying the development of a high-definition image monitor (viewer), an image interpretation of a medical image displayed on a monitor is also made.

In such a case where an image interpretation doctor makes an image interpretation, it is convenient if disease candidate information of a patient as an object of image interpretation can be referred to. Such circumstances being taken into consideration, the applicants of the present invention have proposed a disease candidate information output system capable of outputting disease candidate information for an image of a subject (refer to Japanese Patent Application Publication JP-P2003-325458A). According to the disease candidate information output system disclosed in JP-P2003-325458A, it is possible to determine and output disease candidate information for an image of a subject by searching image data of a similar case in a case database, which stores a large quantity of case image data and diagnostic data related thereto, based on image analysis information of the image of the subject and disease information accompanying the image of the subject.

However, image data and diagnostic data are not always managed in one system (computer) and there are many cases where image data, diagnostic data, other examination information, etc., are stored in respective systems made and sold by different makers and vendors. The disease candidate information output system disclosed in JP-P2003-325458A has taken into consideration the case where disease information accompanies an image of a subject, however, it has not taken into consideration the case where disease information does not accompany an image of a subject, that is, disease information and an image of a subject are managed independently of each other.

SUMMARY OF THE INVENTION

In view of the above-mentioned points, an object of the present invention is to provide an image interpretation report creating apparatus capable of searching cases by combining an image interpretation report and an examination result even when the image interpretation report obtained by examination using a medical image and the examination result obtained by examination using no medical image are stored in different computers, respectively.

In order to achieve the above-mentioned object, an image interpretation report creating apparatus according to one aspect of the present invention is an image interpretation report creating apparatus to be used for creating an image interpretation report when connected directly or via a network to at least one terminal for displaying a medical image, an image server for storing image data of medical images, an image interpretation report server for storing image interpretation report database accumulating image interpretation report data of image interpretation reports created based on medical images, and at least one examination result server for storing examination result database accumulating examination result data of examination results obtained by examination using no medical image, and the apparatus comprises: a display unit for displaying an image interpretation report creation screen for creating an image interpretation report of a medical image obtained by examination using a medical image along with an examination result obtained by examination using no medical image; input means to be used for inputting finding of the medical image and specifying first information and second information in the finding and an examination result displayed on the display unit, respectively; search key generating means for generating at least one first search key for searching the image interpretation report database and at least one second search key for searching the examination result database, based on the first and second information, respectively; search processing means for causing the image interpretation report server to obtain at least one case that matches the at least one first search key and causing the examination result server to obtain at least one case that matches the at least one second search key; similarity degree determining means for determining a degree of similarity between (i) the first and second information specified in the finding and the examination result displayed on the display unit and (ii) the at least one case obtained by the image interpretation report server and the examination result server, and displaying the obtained at least one case in a list on the display unit in an order of the degree of similarity; case display means for displaying contents of a case, which is selected by a user from among the at least one case displayed in the list, on the display unit; and image interpretation report preservation means for causing the image interpretation report server to store image interpretation report data of the image interpretation report created based on the image interpretation report creation screen displayed on the display unit.

According to the present invention, it is possible to display a case in a combination of an image interpretation report and an examination result even when the image interpretation report obtained by examination using a medical image and the examination result obtained by examination using no medical image are stored in different computers, respectively. Consequently, by referring to such a case, a user can shorten the time required for creating an image interpretation report and create an image interpretation report efficiently.

BRIEF DESCRIPTION OF THE DRAWINGS

FIG. 3 is a block diagram showing a configuration of the image interpretation report creating apparatus shown in FIG. 1;

FIG. 4 is a diagram showing an example of data stored in a hard disk shown in FIG. 3;

FIG. 6 is an enlarged view showing an examination information display column, a finding entry column, and a diagnostic result entry column;

FIG. 10 is an enlarged view showing an examination information display column, a finding entry column, and a diagnostic result entry column shown in FIG. 9;

FIG. 11 is an enlarged view showing a blood test result display column shown in FIG. 9;

FIG. 13 is an enlarged view showing a case list display column shown in FIG. 12;

FIG. 15 is an enlarged view showing an examination information display column, a finding display column, and a diagnostic result display column shown in FIG. 14;

FIG. 16 is an enlarged view showing a blood examination result display column shown in FIG. 14;

FIG. 19 is an enlarged view showing a blood test result display column shown in FIG. 18;

FIG. 22 is an enlarged view showing a blood test result display column shown in FIG. 21;

DESCRIPTION OF THE PREFERRED EMBODIMENTS

Figure 1:
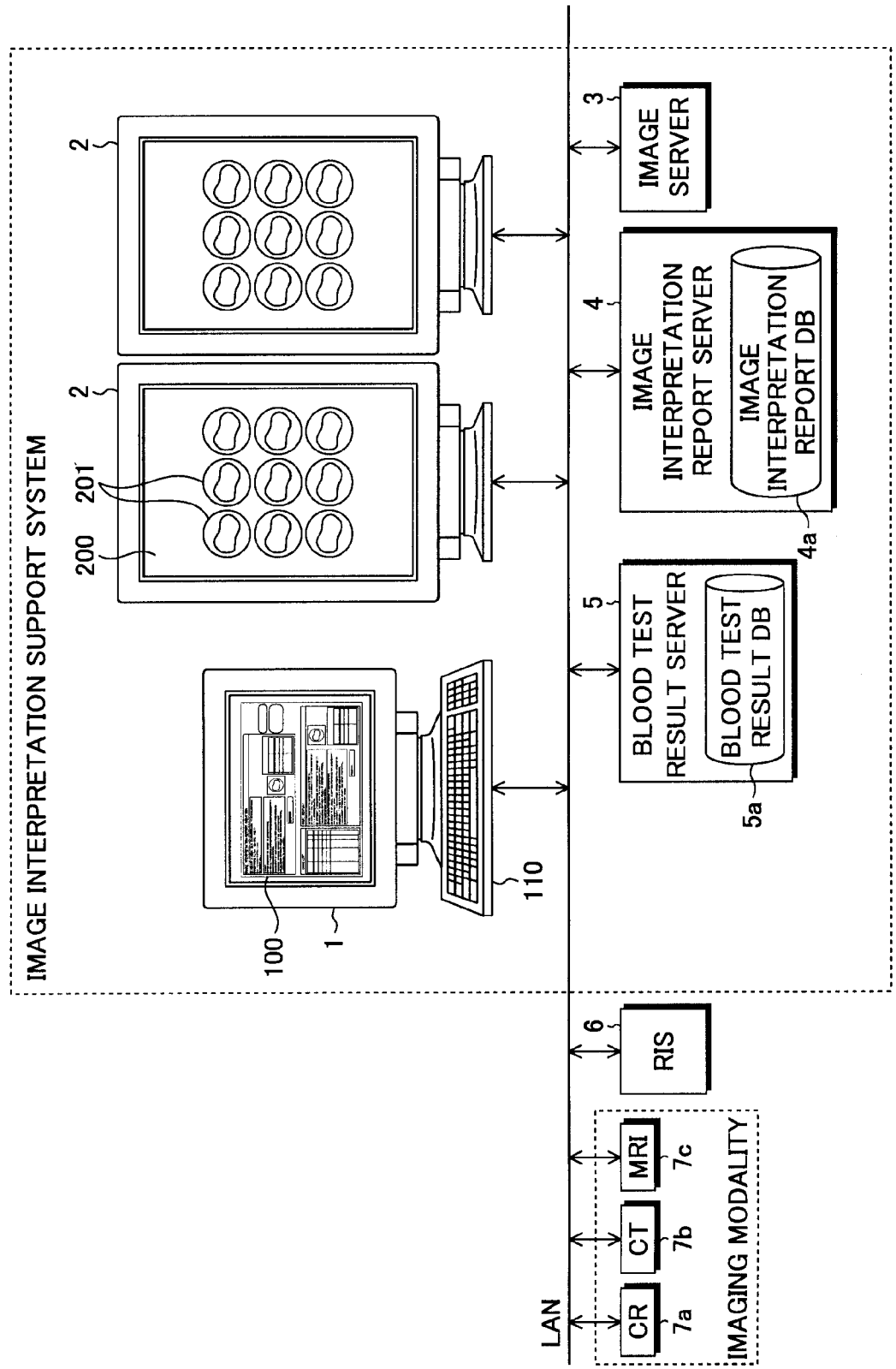
FIG. 1 is a block diagram showing a configuration of an image interpretation support system including an image interpretation report creating apparatus according to one embodiment of the present invention.

Hereinafter, embodiments of the present invention will be described in detail with reference to the drawings. The same reference numerals are assigned to the same components and their explanation will be omitted.

FIG. 1 is a block diagram showing a configuration of an image interpretation support system including an image interpretation report creating apparatus according to one embodiment of the present invention. In the present embodiment, a case where the result of a blood test is utilized will be described as an example of examination using no medical image, however, the present invention is not limited to this and various results of examinations (for example, the result of a urine test, the result of a fecal examination, the result of examination of sputum, the result of pathological examination of a tissue collected from a patient, etc.) can be utilized.

As shown in FIG. 1, the image interpretation support system includes an image interpretation report creating apparatus 1, at least one image display terminal (viewer) 2, an image server 3, an image interpretation report server 4, and a blood test server 5. In addition, the image interpretation support system may be connected to an RIS (radiology information system) 6 and an imaging modality such as a CR apparatus 7a, a CT apparatus 7b, an MRI apparatus 7c, etc. As shown in FIG. 1, these apparatuses are connected to one another via a network, such as a LAN (local area network) etc. Alternatively, the image interpretation report creating apparatus 1 may be connected directly to the image display terminal 2, the image server 3, the image interpretation report server 4, or the blood test result server 5.

Figure 2:
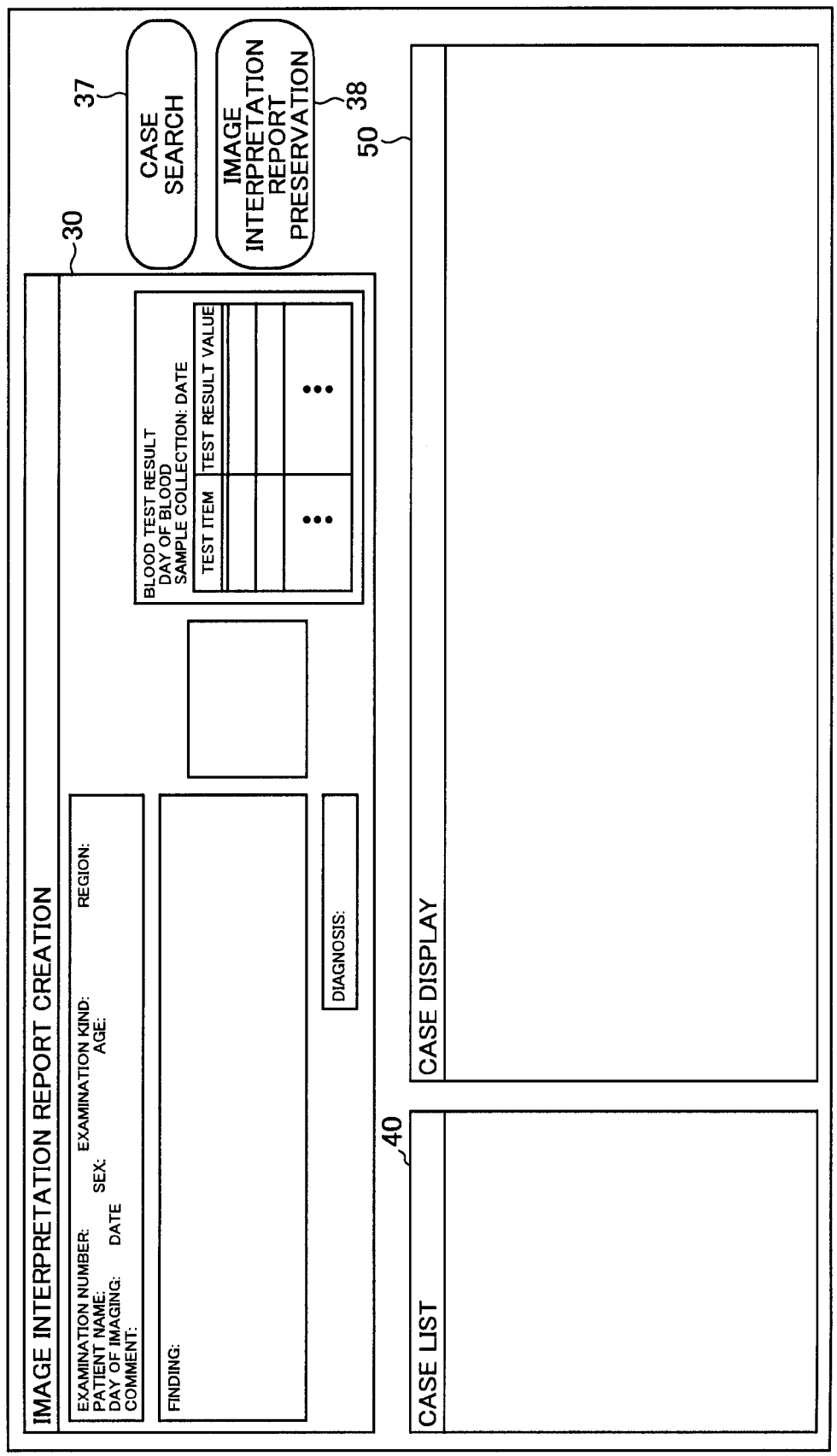
FIG. 2 is a schematic diagram showing an image interpretation report creation screen.

As shown in FIG. 1, the image interpretation report creating apparatus 1 includes a display unit 100 and an input unit 110. The display unit 100 is a display device for displaying an image interpretation report creation screen in which predetermined information entry columns are provided. FIG. 2 shows an image interpretation report creation screen displayed on the display unit 100. The image interpretation report creation screen includes an image interpretation report creation area 30 for an image interpretation doctor to input an image interpretation report, a case search button 37 for causing the image interpretation report creating apparatus 1 to carry out a case search, an image interpretation report preservation button 38 for causing the image interpretation report creating apparatus 1 to preserve an image interpretation report, a case list screen 40 for displaying in a list cases that will serve as references for a diagnosis of a patient as an object of image interpretation, and a case display screen 50 for displaying contents of a case selected by an image interpretation doctor from among the cases displayed in the list. In FIG. 2, these area or screens 30, 40 and 50 are displayed side by side, however, they may overlap in part or in whole. In this case, a user can switch a screen to be displayed at the forefront.

Referring to FIG. 1 again, the input unit 110 is an input device such as a keyboard and a mouse. A user inputs information such as finding text etc. in the input screen displayed on the display unit 100 by using the input unit 110 while observing an examination image displayed on the image display terminal 2.

The image display terminal 2 is a terminal device for displaying an examination image, for which image interpretation is made, and includes a high-definition display. FIG. 1 shows a state in which a plurality of sliced images is displayed in a plurality of frames 201 on a screen 200, respectively. In FIG. 1, the two image display terminals 2 are shown, however, at least one image display terminal 2 may be used, or three or more image display terminals 2 may be used for image interpretation.

The image server 3 is a server for a PACS (picture archiving and communication system) for storing and managing image data acquired by an imaging modality such as, for example, the CR apparatus 7a, the CT apparatus 7b, the MRI apparatus 7c, etc. The image server 3 outputs desired image data to the image interpretation report creating apparatus 1 according to a request of the image interpretation report creating apparatus 1.

The image interpretation report server 4 includes a recording medium for storing image interpretation report database (DB) 4a. The image interpretation report database 4a accumulates image interpretation report data of image interpretation reports created in the past. The image interpretation report data includes an image interpretation report ID, patient ID, patient name, examination ID, text information (finding data) to be displayed as finding by an image interpretation doctor, etc. The image interpretation report server 4 outputs desired image interpretation report data to the image interpretation report creating apparatus 1 according to a request of the image interpretation report creating apparatus 1.

The blood test result server 5 includes a recording medium for storing a blood test result database (DB) 5a. The blood test result database 5a accumulates blood test result data of the results of blood test conducted in the past. The blood test result data includes a patient ID, patient name, examination ID, blood test result, etc. The blood test result server 5 outputs desired blood test result data to the image interpretation report creating apparatus 1 according to a request of the image interpretation report creating apparatus 1.

The RIS 6 is a server for managing the examination of radiation in radiology and manages an examination schedule, orders examination to the imaging modality, and orders an image interpretation of examination for which imaging is finished, that is, image interpretation request, based on patient information, examination contents, etc. entered by using an input terminal. The order for image interpretation is stored in the image interpretation report server 4.

Next, with reference to FIG. 1 and FIG. 3, the configuration of the image interpretation report creating apparatus will be described in detail. FIG. 3 is a block diagram showing the configuration of the image interpretation report creating apparatus shown in FIG. 1. As shown in FIG. 3, the image interpretation report creating apparatus 1 includes, in addition to the display unit 100 and the input unit 110 described above, a central processing unit (hereinafter referred to as CPU) 10, a memory 120 for temporarily storing report data input from the image interpretation report server 4 and image data input from the image server 3, etc., a hard disk control unit 130 for controlling a hard disk 131 as a recording medium, and a network interface 140. These are connected to one another via a bus line. Further, the CPU 10 is connected to a network via the network interface 140.

In the hard disk 131, there are recorded software (programs) for causing the CPU 10 to execute processes, search condition setting data for setting a search condition of an image interpretation report or a blood test result, relation condition setting data for setting a relation condition between an image interpretation report and a blood test, etc. FIG. 4 is a diagram showing an example of the data. FIG. 4 (a) shows an example of the search condition setting data about an image interpretation report, FIG. 4 (b) shows an example of the search condition setting data about a blood test result, and FIG. 4 (c) shows an example of the relation condition setting data. The data may be added, updated, or deleted by a user. The contents and use of the data will be described in detail later. By the way, as a recording medium, other than the built-in hard disk 131, an external hard disk, a flexible disk, MO, MT, RAM, CD-ROM DVD-ROM, etc., may be used.

Next, a plurality of functional blocks constituted by the CPU 10 and software (programs) is described. These functional blocks include a request information acquiring unit 11, an image data acquiring unit 12, an image data output unit 13, an image interpretation report input unit 14, an image interpretation search key generation unit 15, a blood test result search key generation unit 16, an image interpretation report search processing unit 17, a blood test result search processing unit 18, a search result combining unit 19, a similarity degree determining unit 20, a case display unit 21, and an image interpretation report preservation unit 22.

The request information acquiring unit 11 acquires image interpretation request information (also referred to as request information or order information) from the image interpretation report server 4 via a network. The request information includes information about an examination ID, examination image ID, kind of examination, patient name, age and sex of a patient, modality to be used, region to be examined, etc. Alternatively, the request information acquiring unit 11 may acquire request information in an off-line mode, or when the image interpretation report creating apparatus is connected to another system such as a HIS (hospital information system), the request information acquiring unit 11 may acquire request information from such a system via a network.

The image data acquiring unit 12 acquires image data to be displayed on the image display terminal 2 from the image server 3 and supplies it to the image data output unit 13. By the way, in the present embodiment, the image interpretation report creating apparatus 1 acquires image data from the image server 3 in an on-line mode, however, it may also be possible to acquire it from a recording medium such as a DVD (digital versatile disk) and CD (compact disk) in an off-line mode.

The image data output unit 13 outputs image data input from the image data acquiring unit 12 to the image display terminal 2 (FIG. 1) in order to display an examination image on the image display terminal 2. At this time, the image data output unit 13 sets the layout of examination images such that a plurality of sliced images are arranged respectively in the plurality of the frames 201 in the order of the image number, for example.

Figure 5:
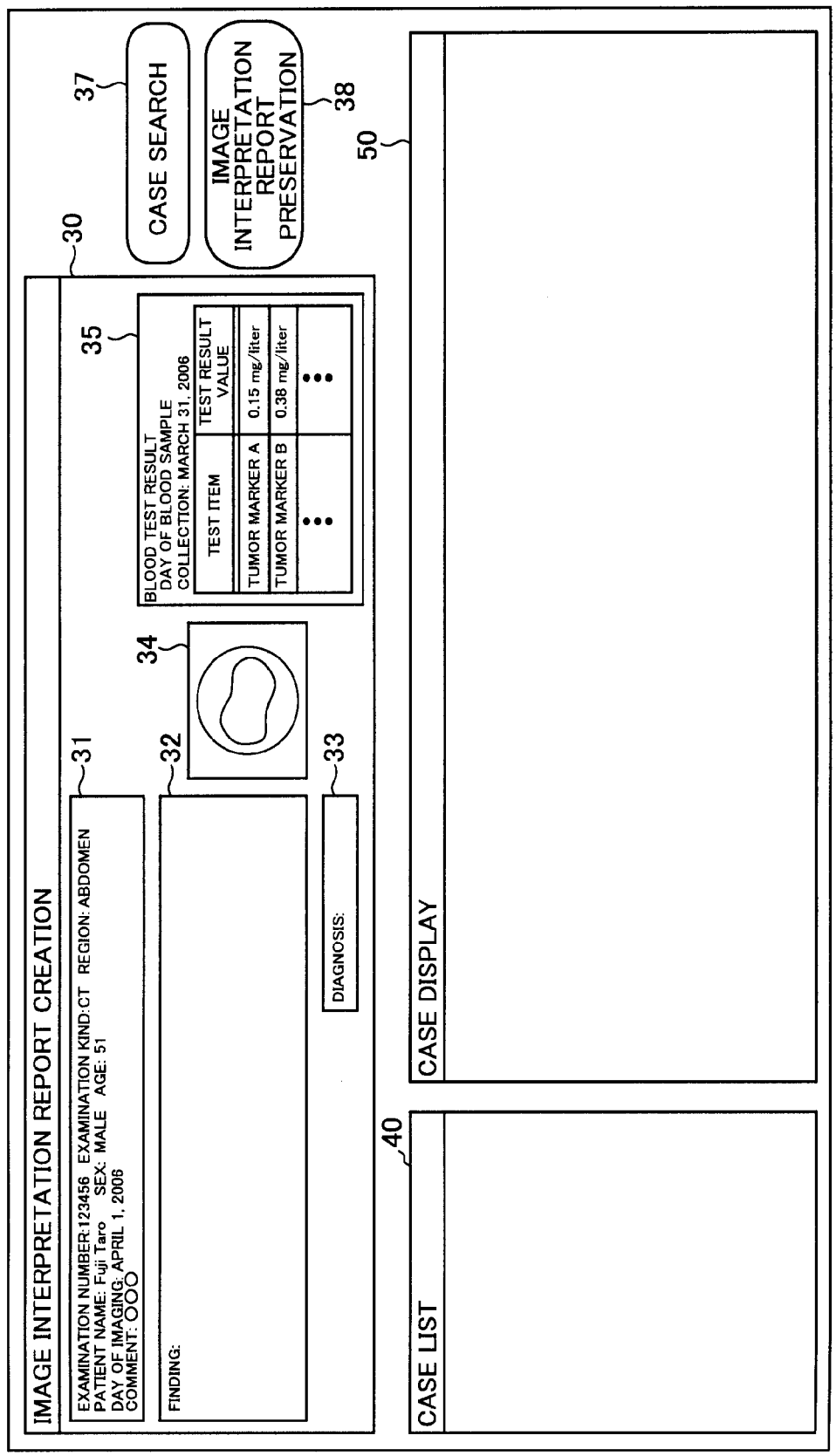
FIG. 5 is a schematic diagram showing an image interpretation report creation screen.

The image interpretation report input unit 14 displays an image interpretation report creation screen on the display unit 100 for an image interpretation doctor to input an image interpretation report. Further, the image interpretation report input unit 14 acquires blood test result data of a patient as an object of image interpretation from the blood test result server 5, when the blood test result data of the patient is accumulated in the blood test result database 5a, and displays it on the display unit 100. By the way, the case where the blood test result data of a patient as an object of image interpretation is not accumulated in the blood test result database 5a will be described later. FIG. 5 shows an example of an image interpretation report creation screen to be displayed on the display unit 100. The image interpretation report creation area 30 includes an examination information display column 31, finding entry column 32, a diagnostic result entry column 33, a key image display column 34, and a blood test result display column 35.

FIG. 6 is an enlarged view of the examination information display column 31, the finding entry column 32, and the diagnostic result entry column 33 shown in FIG. 5. The examination information display column 31 is an area in which information necessary to identify examination such as an examination number, the kind of examination (examination kind), a region to be examined, the name, sex and age of a patient, a comment on the examination, etc., are displayed. The image interpretation report input unit 14 receives the information from the image interpretation report server 4 based on the request information and displays it in the examination information display column 31. Here, the examination number "123456", the examination kind "CT", the region "abdomen", the patient name "Fuji Taro", the sex "male", the age "51", the day of imaging "Apr. 1, 2006", etc., are displayed. The finding entry column 32 is an area in which an image interpretation doctor enters his/her finding. The diagnostic result entry column 33 is an area in which the diagnosis by an image interpretation doctor is entered.

Referring to FIG. 5 again, the key image display column 34 is an area in which an image (key image) determined to be a key for image interpretation by an image interpretation doctor among a series of images obtained by one-time examination is displayed. At least one key image is set for one examination. By the way, as a key image, a sliced image displaying a lesion region in an easy-to-see way, a sliced image displaying a particularly remarkable region, or a sliced image determined to be suitable for image interpretation is selected.

Referring to FIG. 3 again, the search key generating unit including the image interpretation report search key generating unit 15 and the blood test result search key generating unit 16, generates search keys for searching cases that will serve as references for a diagnosis of a patient as an object of image interpretation.

The search processing unit including the image interpretation report search processing unit 17 and the blood test result search processing unit 18, obtains cases that will serve as references for the diagnosis of the patient by using the search keys generated by the search key generating unit.

Specifically, the image interpretation report search key generating unit 15 generates at least one first search key for searching the image interpretation report database 4a (FIG. 1) for at least one case, based on first information specified in the finding displayed on the display unit 100.

The image interpretation report search processing unit 17 causes the image interpretation report server 4 (FIG. 1) to search the image interpretation report database 4a for at least one case that matches the at least one first search key.

The blood test result search key generating unit 16 generates at least one second search key for searching the blood test result database 5a (FIG. 1) for at least one case, based on second information specified in the examination result displayed on the display unit 100.

Further, the blood test result search processing unit 18 adds condition about examination information included in the image interpretation report data in each case obtained by the image interpretation report search processing unit 17 to the at least one second search key to obtain a combined search key such that the blood test result data is related to the image interpretation report data.

Then the blood test result search processing unit 18 causes the blood test result server 5 (FIG. 1) to search the blood test result database 5a for at least one case that matches the combined search key.

The search result combining unit 19 combines the image interpretation report data in each case obtained by the image interpretation report search processing unit 17 and the blood test result data in the related case obtained by the blood test result search processing unit 18.

The similarity degree determining unit 20 makes a determination of a degree of similarity between (i) the first and second information specified in the finding and the examination result displayed on the display unit 100 and (ii) each case obtained by the image interpretation report server 4 and the blood test result server 5 based on the image interpretation report data and the blood test result data combined by the search result combining unit 19, and displays it in a list in the case list screen 40 (FIG. 2, etc.) in a descending order of the degree of similarity.

Specifically, the similarity degree determining unit 20 determines a comprehensive degree of similarity based on (i) a first degree of similarity between the first information specified in the finding displayed on the display unit 100 and each case obtained by the image interpretation report server 4 and (ii) a second degree of similarity between the second information specified in the blood test result displayed on the display unit 100 and each case obtained by the examination result server 5. For example, the similarity degree determining unit 20 determines the comprehensive degree of similarity by adding the first degree of similarity and the second degree of similarity.

The case display unit 21 displays the contents of the case selected by an image interpretation doctor from among the cases displayed in the list in the case list screen 40 in the case display screen 50 (FIG. 2, etc.).

The image interpretation report preservation unit 22 causes the image interpretation report database 4a (FIG. 1) to store the image interpretation report input by the image interpretation doctor.

Figure 7:
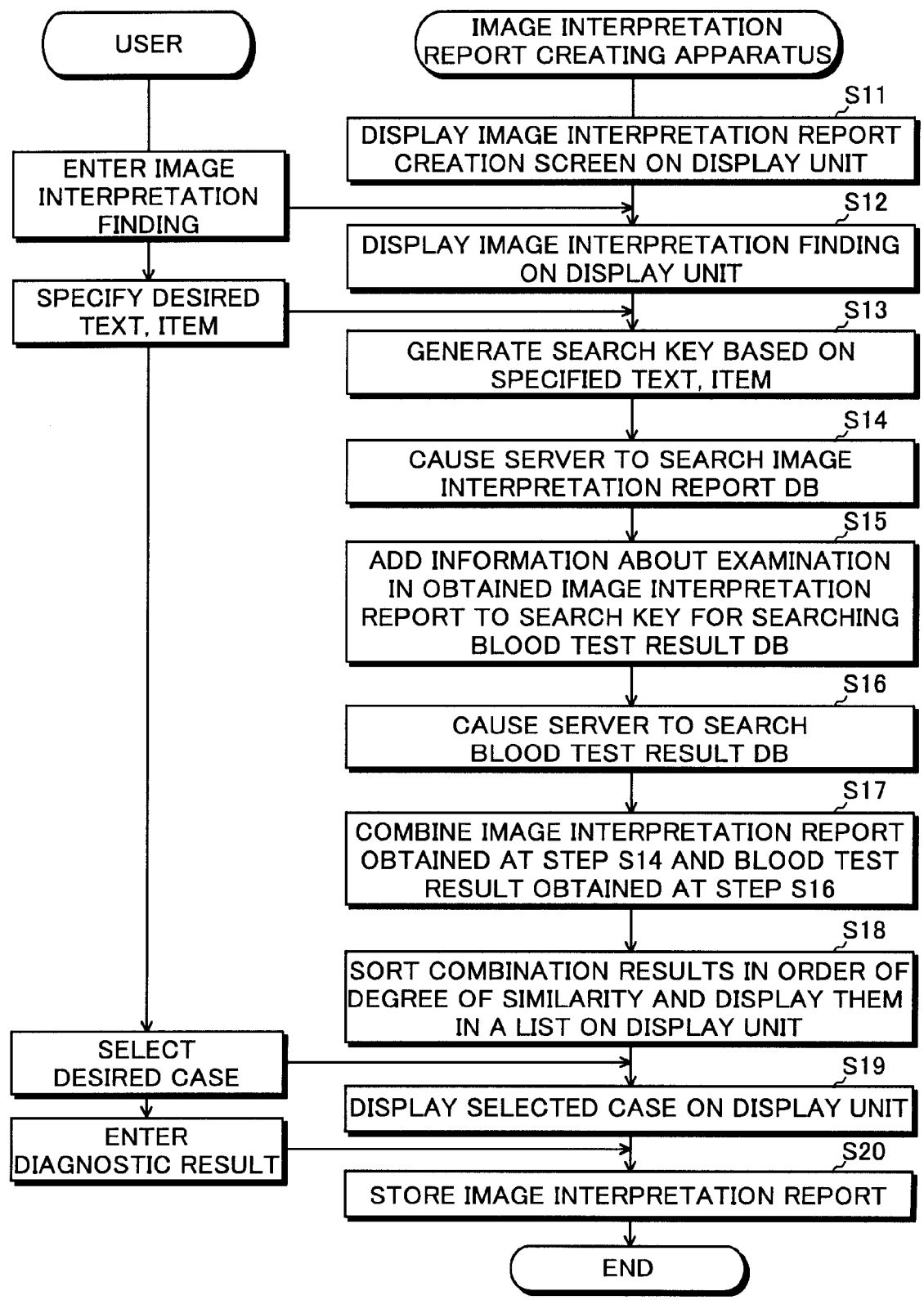
FIG. 7 is a flow chart showing the operation of the image interpretation report creating apparatus shown in FIG. 1.

Next, the operation of the image interpretation report creating apparatus will be described in detail with reference to FIG. 7. FIG. 7 is a flow chart showing the operation of the image interpretation report creating apparatus when the blood test result data of a patient as an object of image interpretation is accumulated in the blood test result database 5a.

By the way, there may be the case where the blood test result data of a patient as an object of image interpretation cannot be obtained from the blood test result server 5 because of the fact that the blood sample of the patient has not yet been collected, that the blood sample has already been collected but the blood test has not yet been done, or that the blood test has already been done but its blood test result data has not yet been accumulated in the blood test result database 5a, etc. Here, the operation of the image interpretation report creating apparatus will be described in the case where the blood test result data of a patient as an object of image interpretation has been accumulated in the blood test result database 5a and the blood test result data can be obtained from the blood test result server 5. The operation of the image interpretation report creating apparatus in the case where the blood test result data of a patient as an object of image interpretation has not yet been accumulated in the blood test result database 5a and the blood test result data of the patient as an object of image interpretation cannot be obtained from the blood test result server 5 will be described later.

The request information acquiring unit 11 of the image interpretation report creation unit 1 starts the operation upon receipt of request information via a network, the image data acquiring unit 12 acquires image data from the image server 3 (FIG. 1), and the image data output unit 13 outputs the image data acquired by the image data acquiring unit 12 to the image display terminal 2 (FIG. 1) to display the image. On the other hand, the image interpretation report creating apparatus 1 displays the image interpretation report creation screen shown in FIG. 5 on the display unit 100 (step S11). Alternatively, the image interpretation report creation screen 1 may display a work list on the display unit 100 when a user logs in and display the image interpretation report creation screen relating to the examination selected from the work list by the user.

Figure 8:
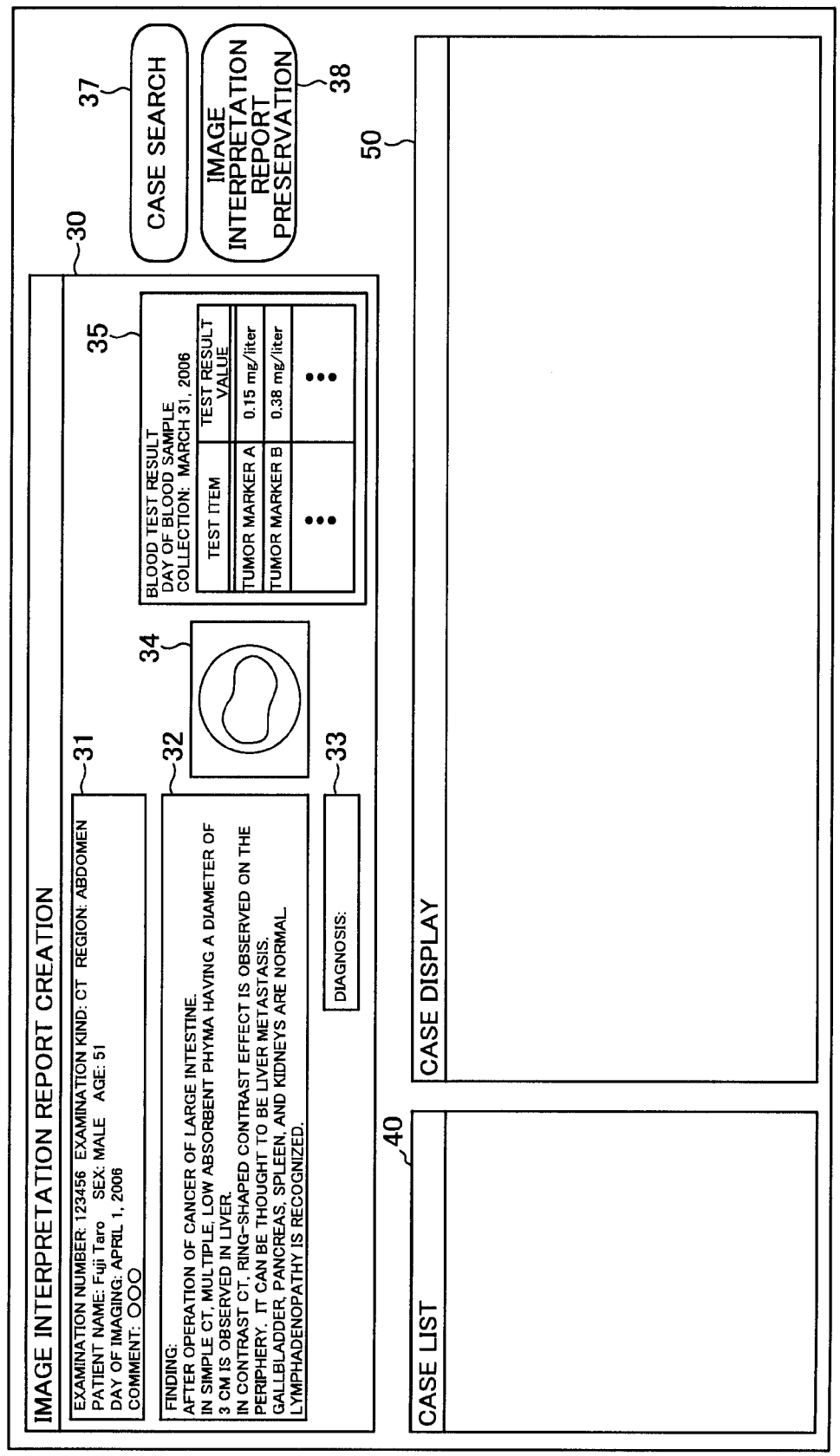
FIG. 8 is a schematic diagram showing an image interpretation report creation screen.

An image interpretation doctor enters his/her finding while watching the image displayed on the image display terminal 2 (FIG. 1). The entered finding is displayed in the finding entry column 32 (step S12). FIG. 8 is a diagram showing an example of the image interpretation report creation screen in which the image interpretation doctor has entered his/her finding.

By the way, when entering his/her finding, an image interpretation doctor can set a key image as an image that the image interpretation doctor has determined to be a key for image interpretation among the series of images obtained by one-time examination. When a key image has been set, the set key image is displayed in the key image display column 34. As a key image, a sliced image displaying a lesion region in an easy-to-see way, a sliced image displaying a particularly remarkable region, or a sliced image determined to be suitable for image interpretation is selected. In addition, it may also be possible to set, when a key image has been set, a link between the key image displayed in the key image display column 34 and the examination image displayed on the image display terminal 2 (FIG. 1). When a link has been set, the image data output unit 13 may set a layout of the examination images in accordance with the operation of the user, that is, the key image is selected by clicking with a mouse etc. For example, the key image may be arranged in the central frame of the screen 200.

When the image interpretation doctor selects the blood test from among various examinations using no medical image, the blood test items are displayed on the display unit 100.

Figure 9:
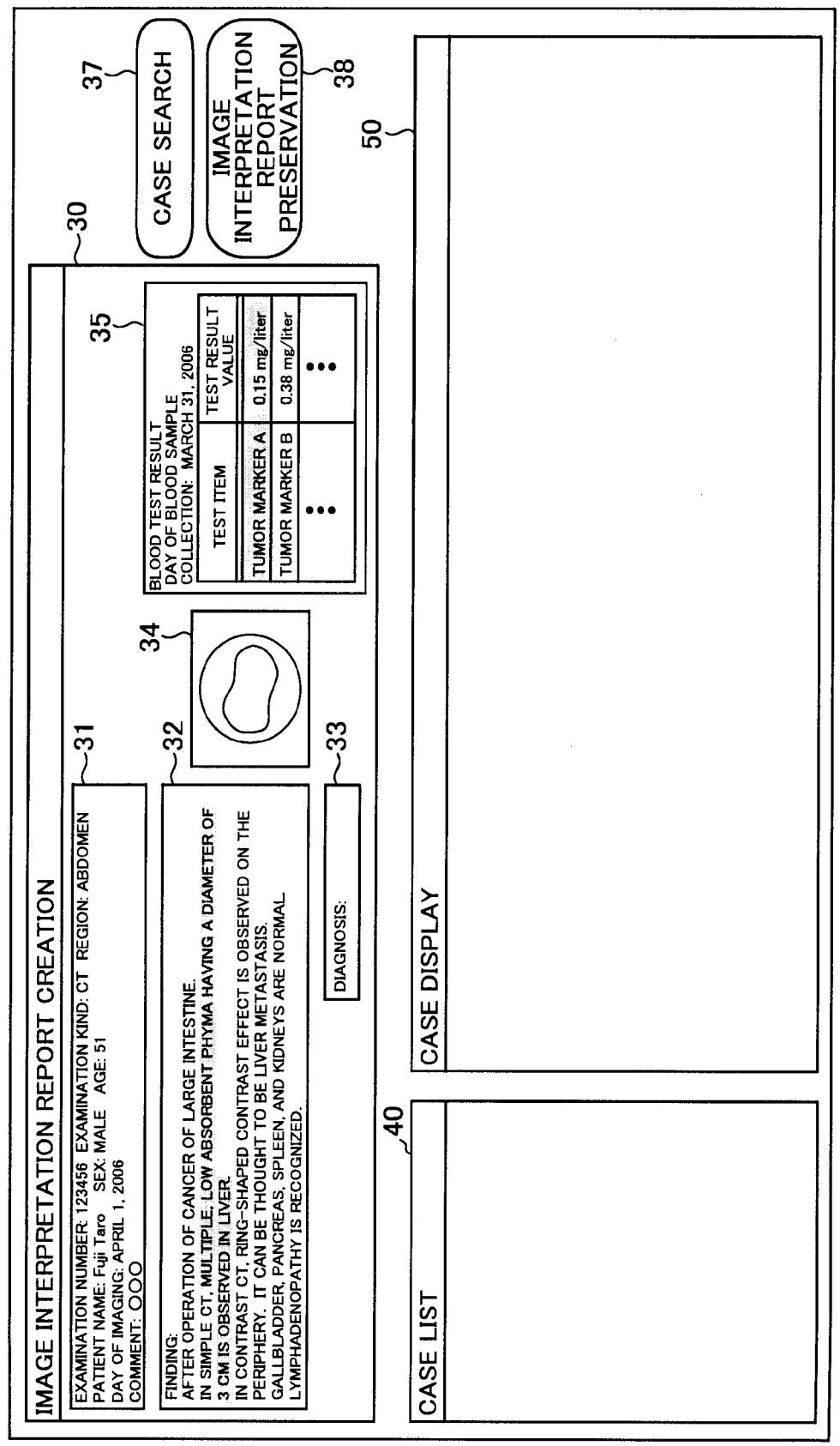
FIG. 9 is a schematic diagram showing an image interpretation report creation screen.

Next, the image interpretation doctor specifies at least one part or the whole of the finding input by himself/herself and the desired blood test item by using a mouse. FIG. 9 is a diagram showing the case where a part of the finding and one of the blood test items have been specified.

FIG. 10 is an enlarged view of the finding entry column 32, etc. shown in FIG. 9. In the finding entry column 32, the finding that "After operation of cancer of large intestine. In simple CT, multiple, low absorbent phyma having a diameter of 3 cm is observed in liver. In contrast CT, ring-shaped contrast effect is observed on the periphery. It can be thought to be liver metastasis. Gallbladder, pancreas, spleen, and kidneys are normal. Lymphadenopathy is recognized" is entered. As shown in FIG. 10, a part of the finding "multiple, low absorbent phyma having a diameter of 3 cm is observed in liver" is specified and shown in a shaded display.

FIG. 11 is an enlarged view of the blood test result display column 35 shown in FIG. 9. The blood test result display column 35 includes an area in which the blood test result of a patient as an object of image interpretation (here, "Fuji Taro") is displayed. Here, the day of blood sample collection "Mar. 31, 2006" is displayed, and the examination item "tumor marker A" and its examination result value "0.15 mg/liter", the examination item "tumor marker B" and its examination result value "0.38 mg/liter", etc., are displayed. As shown in FIG. 11, the blood test item "tumor marker A" and its value "0.15 mg/liter" are specified and shown in a shaded display. By the way, at this time, it may also be possible to specify the examination information in the examination information display column 31 (FIG. 9) together.

Then, when the image interpretation doctor clicks the case search button 37 (FIG. 9) in the image interpretation report creation screen, the image interpretation report search key generating unit 15 generates a search key for searching the image interpretation report database 4a (FIG. 1) based on at least one part or the whole of the finding specified by the image interpretation doctor. Further, the blood test result search key generating unit 16 generates a search key for searching the blood test result database 5a (FIG. 1) based on the blood test item and its value specified by the image interpretation doctor (step S13).

Specifically, the image interpretation report search key generating unit 15 extracts a keyword from the finding specified by the image interpretation doctor, analyzes it by replacing the words with general words etc., and collates its result with the search condition setting data (FIG. 4 (*a*)). Here, the keyword of the analysis result of the part of the finding selected by the image interpretation doctor "multiple, low absorbent phyma having a diameter of 3 cm is observed in liver" (refer to the finding entry column 32 in FIG. 10) matches the keyword "phyma in liver" in the first field of the first record in the search condition setting data (FIG. 4 (*a*)) in a high correlation therebetween. Further, in the second field of the first record of the search condition setting data (FIG. 4 (*a*)), the condition that "±1 cm as to diameter" is stored. Then, the image interpretation report search key generating unit 15 therefore generates "phyma in liver" and "diameter 2 cm to 4 cm" as a search key.

On the other hand, the blood test item "tumor marker A" (refer to the blood test result display column 35 in FIG. 11) selected by the image interpretation doctor matches the examination item "tumor marker A" in the first field of the first record in the search condition setting data (FIG. 4 (*b*)). Further, in the second field of the first record in the search condition setting data (FIG. 4 (*b*)), the condition that "±0.01 mg/liter" is stored. The blood test result search key generating unit 16 therefore generates "tumor marker A" and "0.14 mg/liter to 0.16 mg/liter" as a search key.

Next, the image interpretation report search processing unit 17 causes the image interpretation report server 4 to search the image interpretation report database 4a by using the search key generated by the image interpretation report search key generating unit 15 (step S14). Here, the image interpretation report search processing unit 17 causes the image interpretation report server 4 to obtain an image interpretation report of a patient having a phyma with a diameter of 2 cm to 4 cm in the liver so as to obtain an image interpretation report that meets such a condition. The image interpretation report search processing unit 17 outputs information about the examination (examination number, examination kind, region, patient ID, patient name, etc.) in the image interpretation report obtained as a search result to the blood test result search processing unit 18.

The blood test result search processing unit 18 adds at least one part or the whole of the information about the examination output from the image interpretation report search processing unit 17 as a search key to the search key generated by the blood test result search key generating unit 16 (step S15). By adding the information about the examination output from the image interpretation report search processing unit 17 as a search key, it is possible to winnow out, for example, the blood test results of the patients etc. for whom the blood test has been done but the image examination has not been done. Further, the blood test result search processing unit 18 adds the contents of the relation condition setting data (FIG. 4 (*c*)) as a search key. In FIG. 4 (*c*), as a relation condition, "interval between the day of imaging and the day of blood sample collection is not more than seven days" has been set. By adding the relation condition as a search key, it is possible to winnow out the blood test results that have been done independently of the image examination.

Then, at step S16, the blood test result search processing unit 18 causes the blood test result server 5 to search the blood test result database 5a by using the search key obtained at step S15. Here, the blood test result search processing unit 18 causes the blood test result server 5 to obtain the blood test result of a patient who is an object of the image interpretation report obtained by the image interpretation report search processing unit 17 and whose tumor marker A value is 0.14 mg/liter to 0.16 mg/liter so as to obtain a blood test result that meets such a condition.

Next, at step S17, the search result combining unit 19 combines the image interpretation report obtained by the image interpretation report search processing unit 17 at step S14 and the blood test result obtained by the blood test result search processing unit 18 at step S16.

Figure 12:
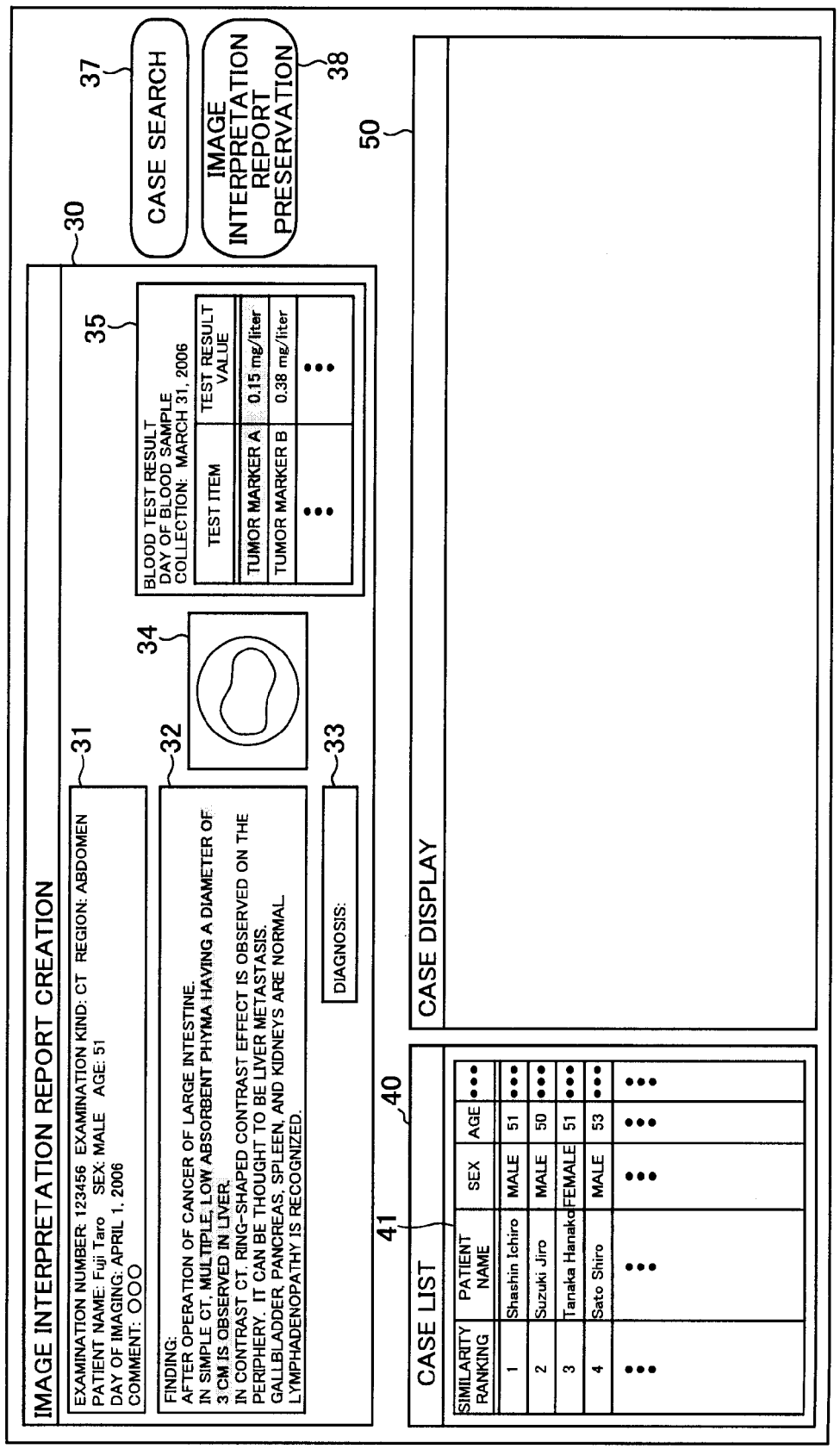
FIG. 12 is a schematic diagram showing an image interpretation report creation screen.

Then, the similarity degree determining unit 20 sorts the combination results of the search result combining unit 19 in the order of the degree of similarity and displays them in a list in the case list display column 40 in the image interpretation report creation screen (step S18). FIG. 12 is a diagram showing an example of the image interpretation report creation screen at this time, and FIG. 13 is an enlarged view of the case list display column 41 in FIG. 12. As shown in FIG. 13, in the case list display column 41, the similarity ranking, patient name, sex, age, etc., are displayed in a list in the order of the degree of similarity. By the way, it is possible to realize the determination of the degree of similarity by using an accumulated value obtained by performing a predetermined weighting to each item and accumulating them, or by carrying out a morphemic analysis, a clause analysis or a dependency analysis, etc., as widely known generally.

Figure 14:
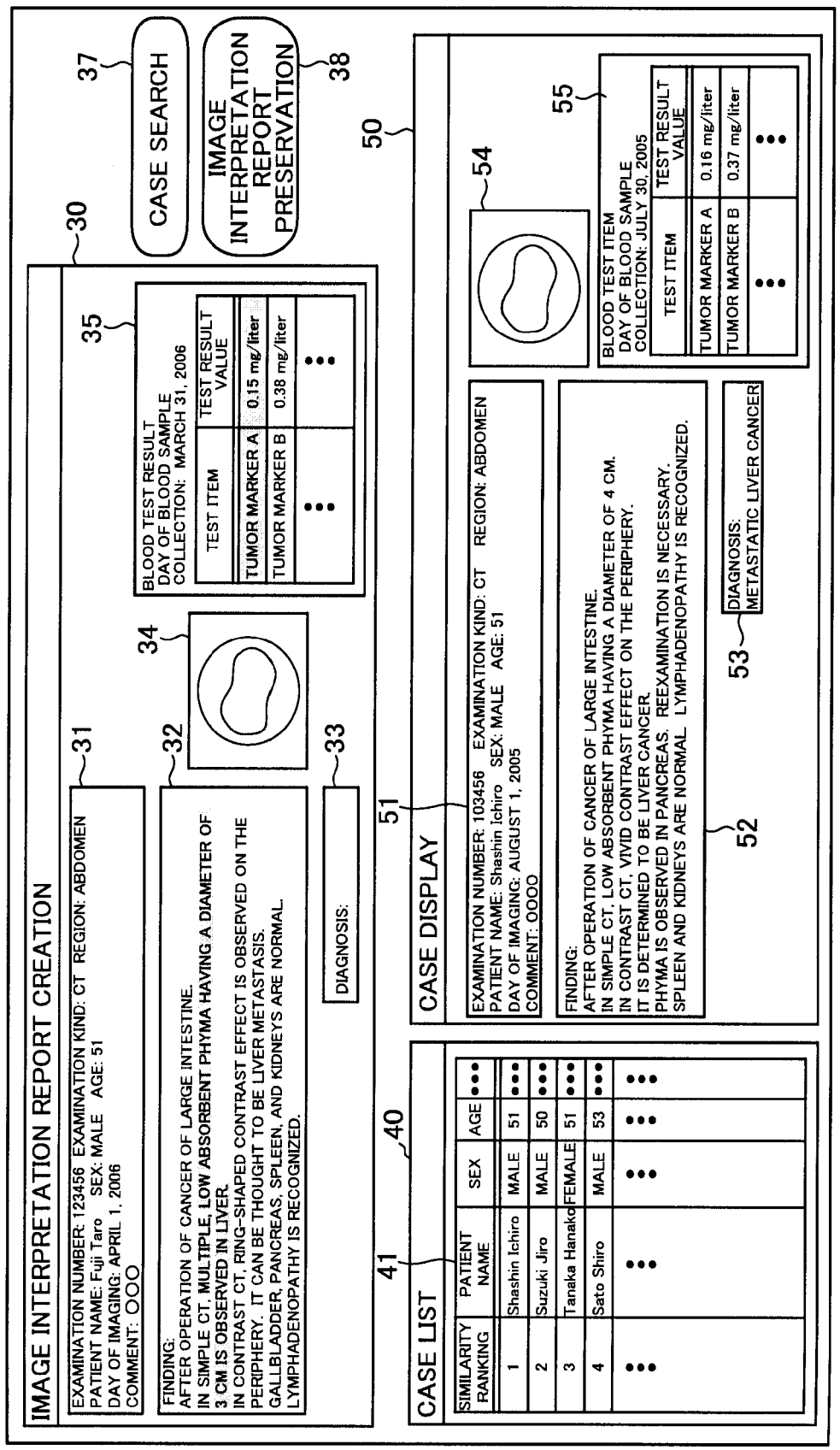
FIG. 14 is a schematic diagram showing an image interpretation report creation screen.

The image interpretation doctor selects a desired case from among the cases displayed in a list in the case list display column 41 by using a mouse. The case display unit 21 displays the contents of the case selected by the image interpretation doctor in the case display column 50 on the display unit 100 (step S19). Here, it is assumed that the image interpretation doctor selects the case of the patient name "Shashin Ichiro". FIG. 14 is a diagram showing an example of the image interpretation report creation screen at this time, and FIG. 15 and FIG. 16 are enlarged views of the case display column shown in FIG. 14. As shown in FIG. 14, the case display column 50 has an examination information display column 51 for displaying examination information of the case selected by the image interpretation doctor (the examination number and the kind of examination necessary to identify the examination, the region to be examined, the name, sex, and age of the patient, a comment about the examination etc.), a finding display column 52 for displaying his/her finding, a diagnostic result display column 53 for displaying a diagnostic result, a key image display column 54 for displaying a key image, and a blood test result display column 55 for displaying a blood test result.

By the way, the image interpretation doctor can repeat the search cases until a case that will serve as a reference for a diagnosis of the patient as an object of image interpretation is obtained. This can be realized by the repetition of steps S13 to S18 shown in FIG. 8 by the image interpretation report creating apparatus 1.

In addition, the image interpretation doctor can repeat the selection of a case from among the cases displayed in a list until a case that will serve as a reference for a diagnosis of the patient as an object of image interpretation is obtained. This can be realized by the repetition of step S19 shown in FIG. 8 by the image interpretation report creating apparatus 1.

When a case that will serve as a reference for a diagnosis of the patient is displayed, the image interpretation doctor inputs the diagnostic result in the diagnostic result entry column 33 with reference to the case. Then, when the image interpretation doctor clicks the image interpretation report preservation button 38 (FIG. 14, etc.) in the image interpretation report creation screen, the image interpretation report preservation unit 22 causes the image interpretation report server 4 to store the image interpretation report in the image interpretation report database 4a (step S20).

As described above, according to the image interpretation report creating apparatus of the present embodiment, it is possible to display a case that is a combination of an image interpretation report and a blood test result even if the image interpretation report database 4a and the blood test result database 5a are stored in different servers (computers). By referring to such a case, the image interpretation doctor can easily make a diagnosis.

Figure 17:
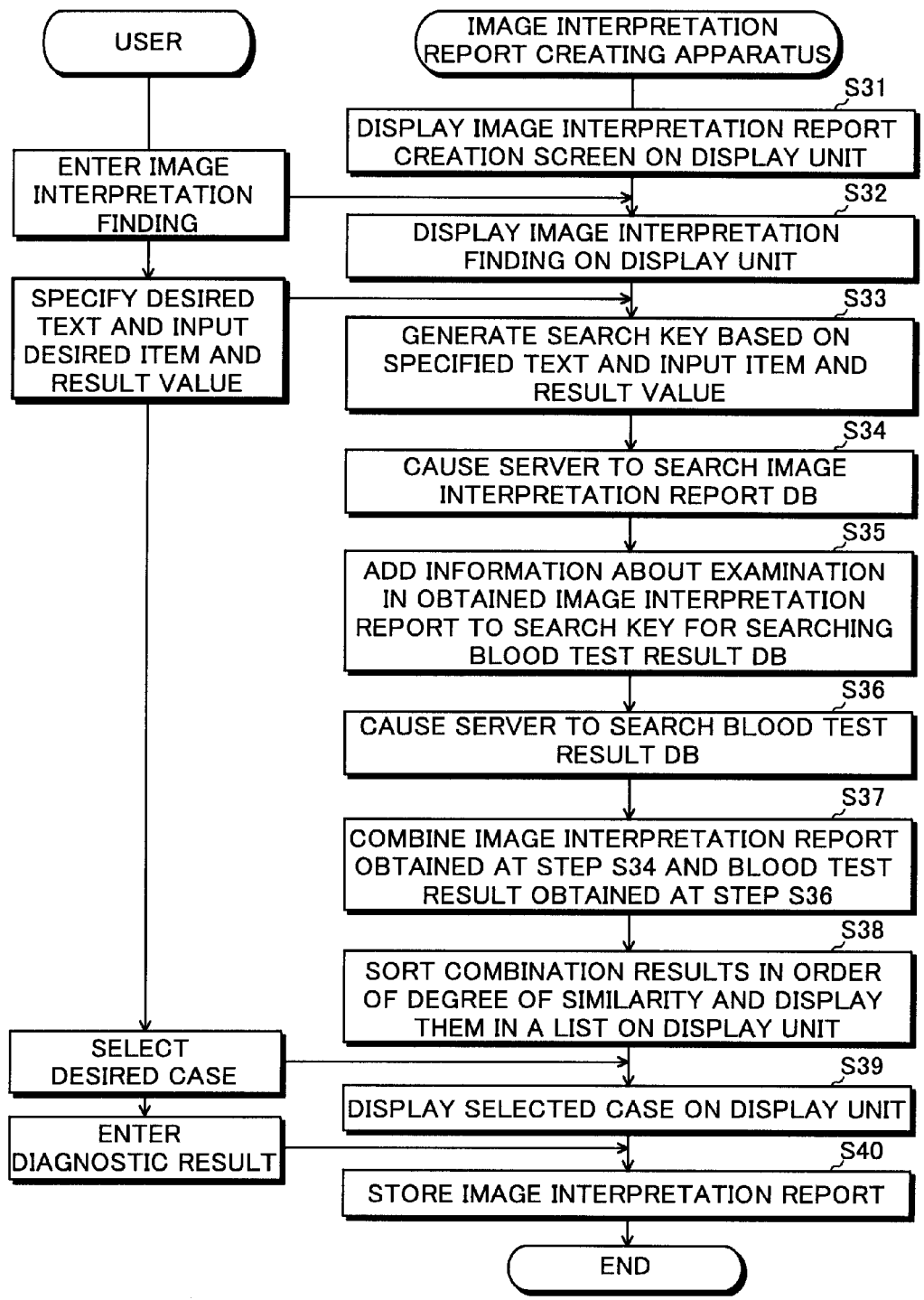
FIG. 17 is a flow chart showing the operation of the image interpretation report creating apparatus shown in FIG. 1.

Next, the operation of the image interpretation report creating apparatus in the case where the blood test result data of a patient as an object of image interpretation has not yet been accumulated in the blood test result database 5a will be described in detail. FIG. 17 is a flow chart showing the operation of the image interpretation report creating apparatus in the case where the blood test result data of a patient as an object of image interpretation has not yet been accumulated in the blood test result database 5a.

When the request information acquiring unit 11 of the image interpretation report creating apparatus 1 receives request information via a network, the operation starts and the image data acquiring unit 12 acquires image data from the image server 3 (FIG. 1), and the image data output unit 13 outputs the image data acquired by the image data acquiring unit 12 to the image display terminal 2 (FIG. 1) to display the image. On the other hand, the image interpretation report input unit 14 displays the image interpretation report creation screen shown in FIG. 18 on the display unit 100 (step S31).

Figure 18:
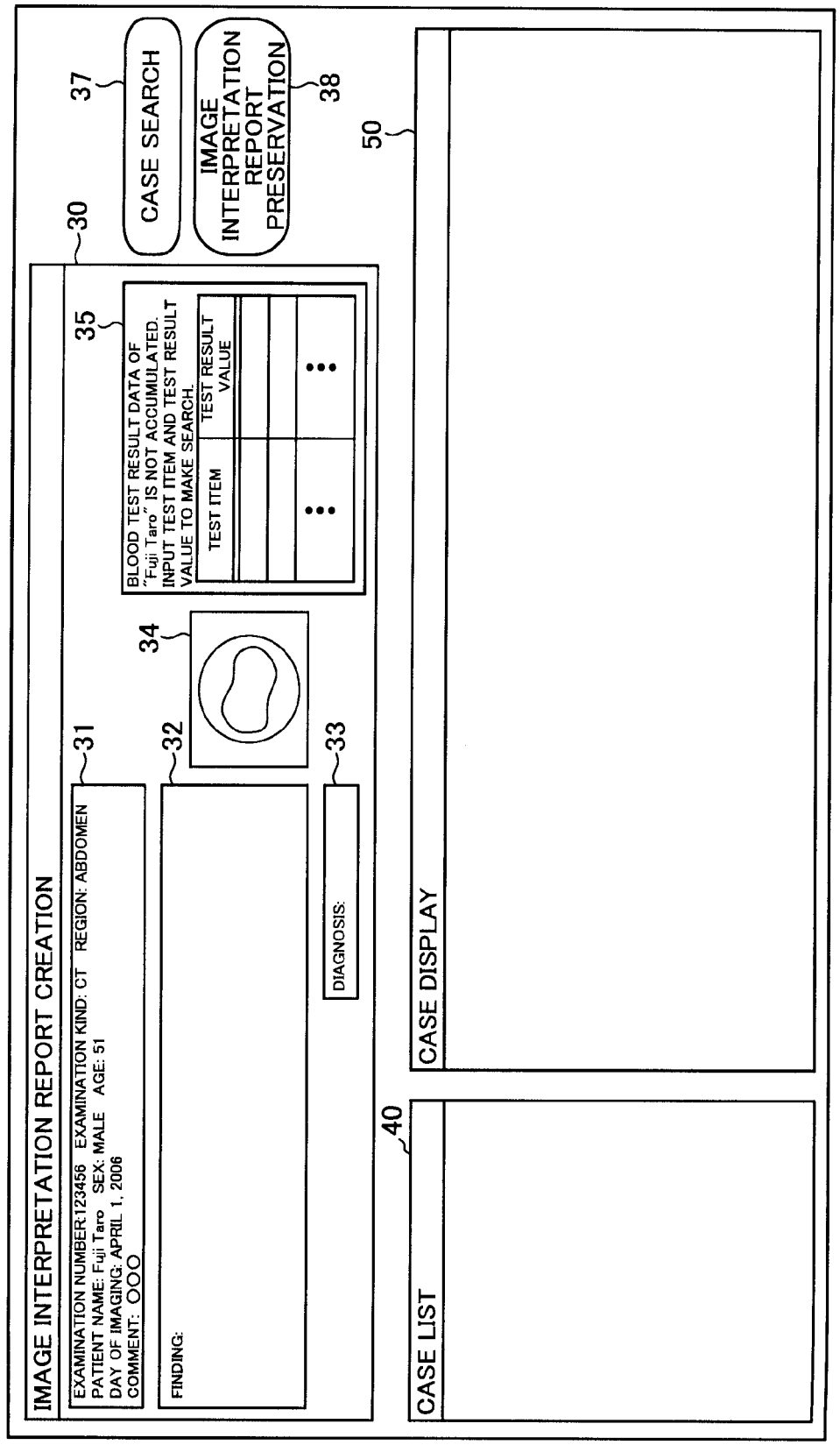
FIG. 18 is a schematic diagram showing an image interpretation report creation screen.

In the case where the blood test result data of a patient as an object of image interpretation (here, "Fuji Taro") is accumulated in the blood test result database 5a, the blood test result of the patient ("Fuji Taro") is displayed in the blood test result display column 35 in the image interpretation report creation screen as shown in FIG. 5 described above. On the other hand, in the case where the blood test result data of the patient ("Fuji Taro") is not accumulated in the blood test result database 5a, a message to notify the image interpretation doctor that the blood test result data of the patient ("Fuji Taro") is not accumulated in the blood test result database 5a is displayed in the blood test result display column 35 in the image interpretation report creation screen as shown in FIG. 18. FIG. 19 is an enlarged view of the blood test result display column 35 shown in FIG. 18.

Figure 20:
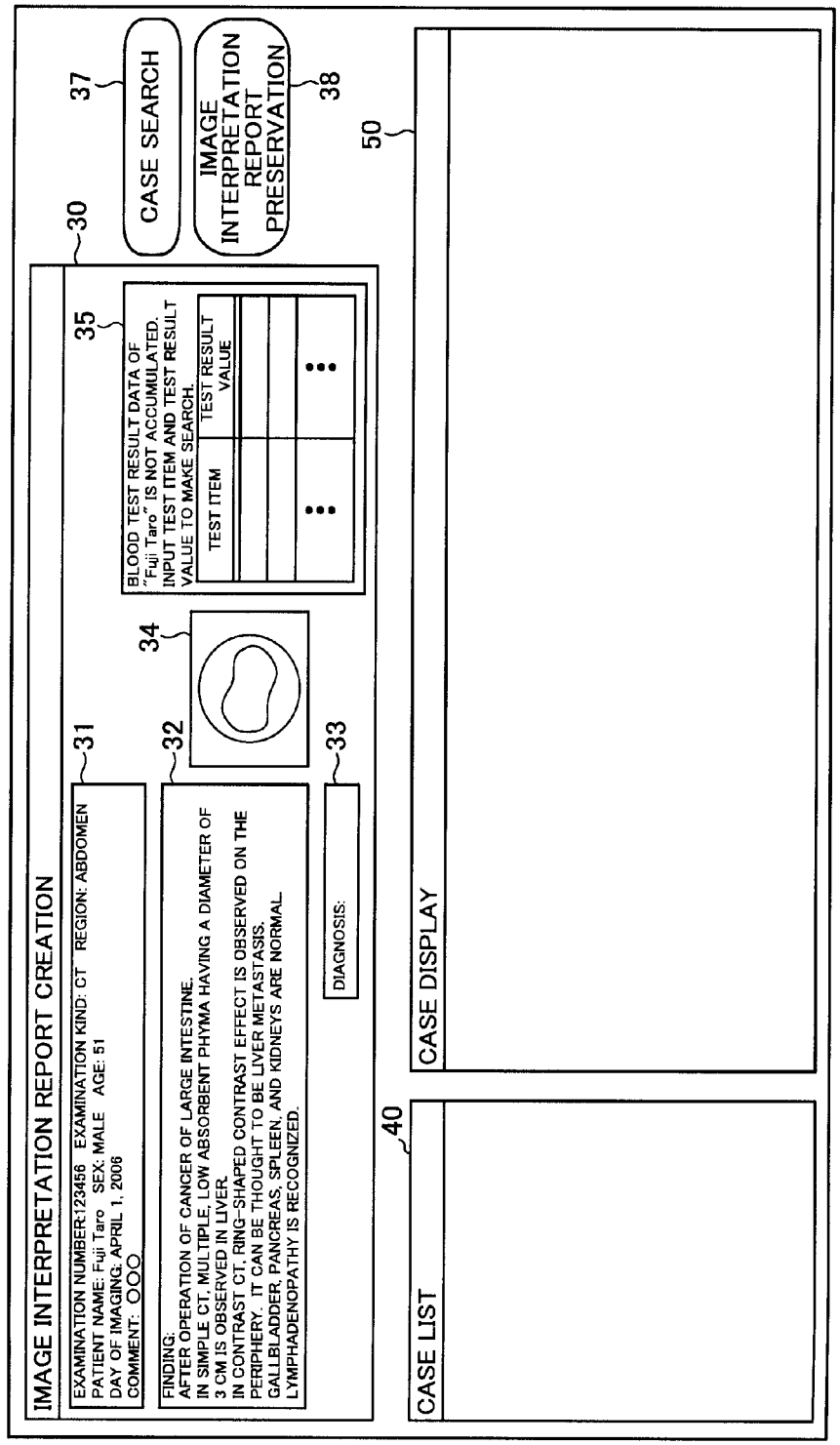
FIG. 20 is a schematic diagram showing an image interpretation report creation screen.

The image interpretation doctor enters his/her finding while watching the image displayed on the image display terminal 2 (FIG. 1). The entered finding is displayed in the finding entry column 32 (step S32). FIG. 20 is a diagram showing an example of the image interpretation report creation screen in which the image interpretation doctor has entered his/her finding.

Figure 21:
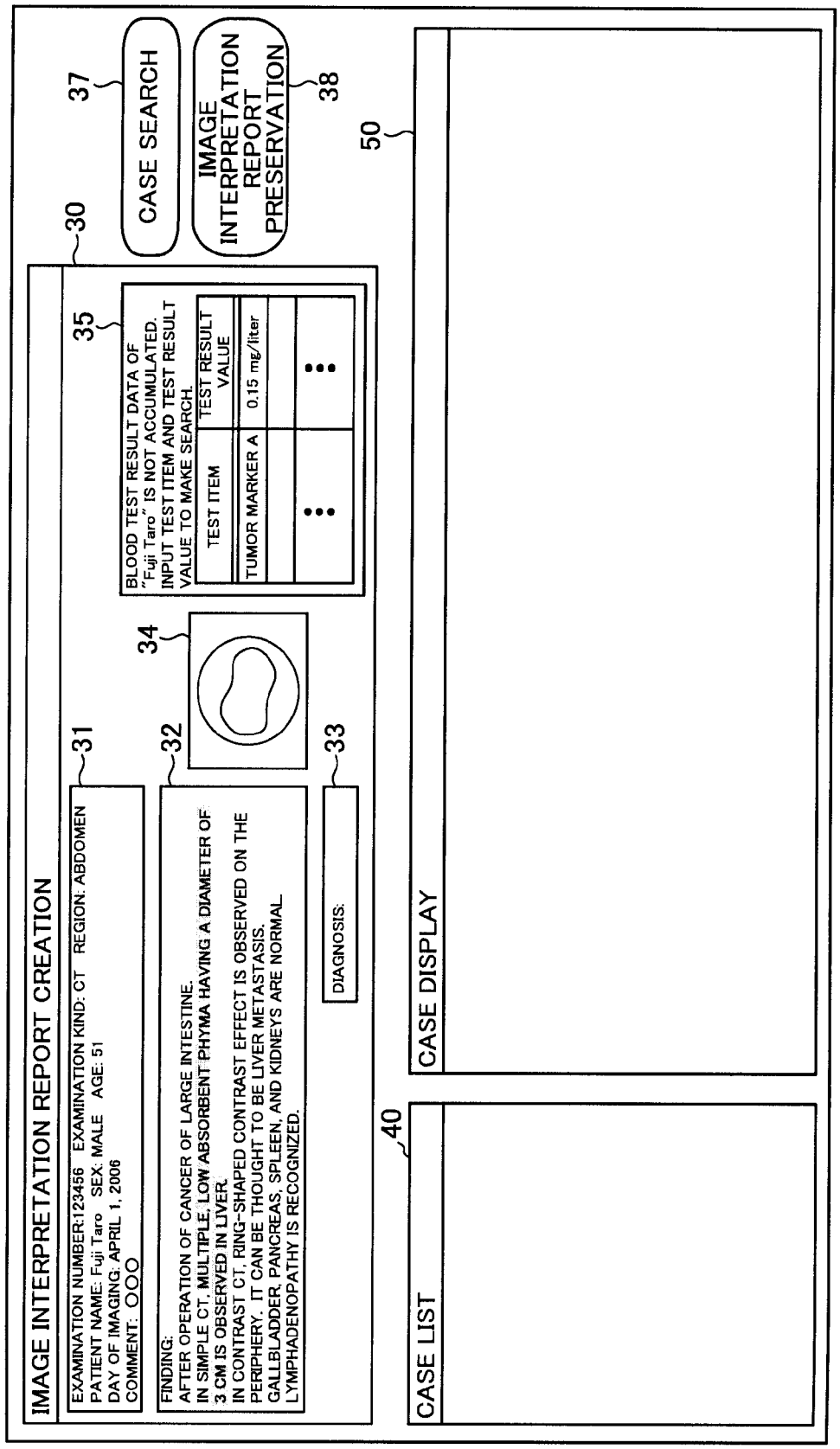
FIG. 21 is a schematic diagram showing an image interpretation report creation screen.

Next, the image interpretation doctor specifies at least one part or the whole of the finding entered by himself/herself by using a mouse and enters a desired blood test item and values by using a keyboard as information to be used for generating a search key. By the way, the blood test result item and the values may be selected and input by using a pull down menu. FIG. 21 is a diagram showing a screen in which a part of the finding is specified and a set of blood test items and values is input. The finding text entered in the finding entry column 32 shown in FIG. 21 and the part of the finding text specified by the image interpretation doctor are the same as those in FIG. 10.

FIG. 22 is an enlarged view of the blood test result display column 35 shown in FIG. 21. In the first row of the examination item field in the blood test result display column 35, an examination item such as "tumor marker A" has been input. In addition, in the first row of the examination result value field in the blood test result display column 35, a value such as "0.15 mg/liter" has been input. By the way, it may also be possible to input two or more sets of examination items and values although one set of examination items and values is input here.

Then, when the image interpretation doctor clicks the case search button 37 (FIG. 21) in the image interpretation report creation screen, the image interpretation report search key generating unit 15 generates at least one search key for searching the image interpretation report database 4a (FIG. 1) based on at least one part or the whole of the finding specified by the image interpretation doctor. Further, the blood test result search key generating unit 16 generates at least one search key for searching the blood test result database 5a (FIG. 1) based on the blood test item and its value input by the image interpretation doctor (step S33).

Here, the blood test item "tumor marker A" (refer to the blood test result display column 35 in FIG. 22) input by the image interpretation doctor matches the examination item "tumor marker A" in the first field of the first record in the search condition setting data (FIG. 4 (*b*)). Further, in the second field of the first record in the search condition setting data (FIG. 4 (*b*)), the condition that "±0.01 mg/liter" is stored. The blood test result search key generating unit 16 therefore generates "tumor marker A" and "0.14 mg/liter to 0.16 mg/liter" as a search key.

Next, the image interpretation report search processing unit 17 causes the image interpretation report server 4 to search the image interpretation report database 4a by using the search key generated by the image interpretation report search key generating unit 15 (step S34).

The blood test result search processing unit 18 adds at least one part or the whole of the information about the examination output from the image interpretation report search processing unit 17 as a search key to the search key generated by the blood test result search key generating unit 16 (step S35). By adding the information about the examination output from the image interpretation report search processing unit 17 as a search key, it is possible to winnow out, for example, the blood test results of the patients etc. for whom the blood test has been done but the image examination has not been done. Further, the blood test result search processing unit 18 adds the contents of the relation condition setting data (FIG. 4 (*c*)) as a search key. In FIG. 4 (*c*), as a relation condition, "interval between the day of imaging and the day of blood sample collection is not more than seven days" has been set. By adding the relation condition as a search key, it is possible to winnow out the blood test results that have been done independently of the image examination.

Then, at step S36, the blood test result search processing unit 18 causes the blood test result server 5 to search the blood test result database 5a by using the search key obtained at step S35. Here, the blood test result search processing unit 18 causes the blood test result server 5 to obtain the blood test result of a patient who is an object of the image interpretation report obtained by the image interpretation report search processing unit 17 and whose tumor marker A value is 0.14 mg/liter to 0.16 mg/liter so as to obtain a blood test result that meets such a condition.

Next, the search result combining unit 19 combines the image interpretation report obtained by the image interpretation report search processing unit 17 and the blood test result obtained by the blood test result search processing unit 18 (step S37).

Figure 23:
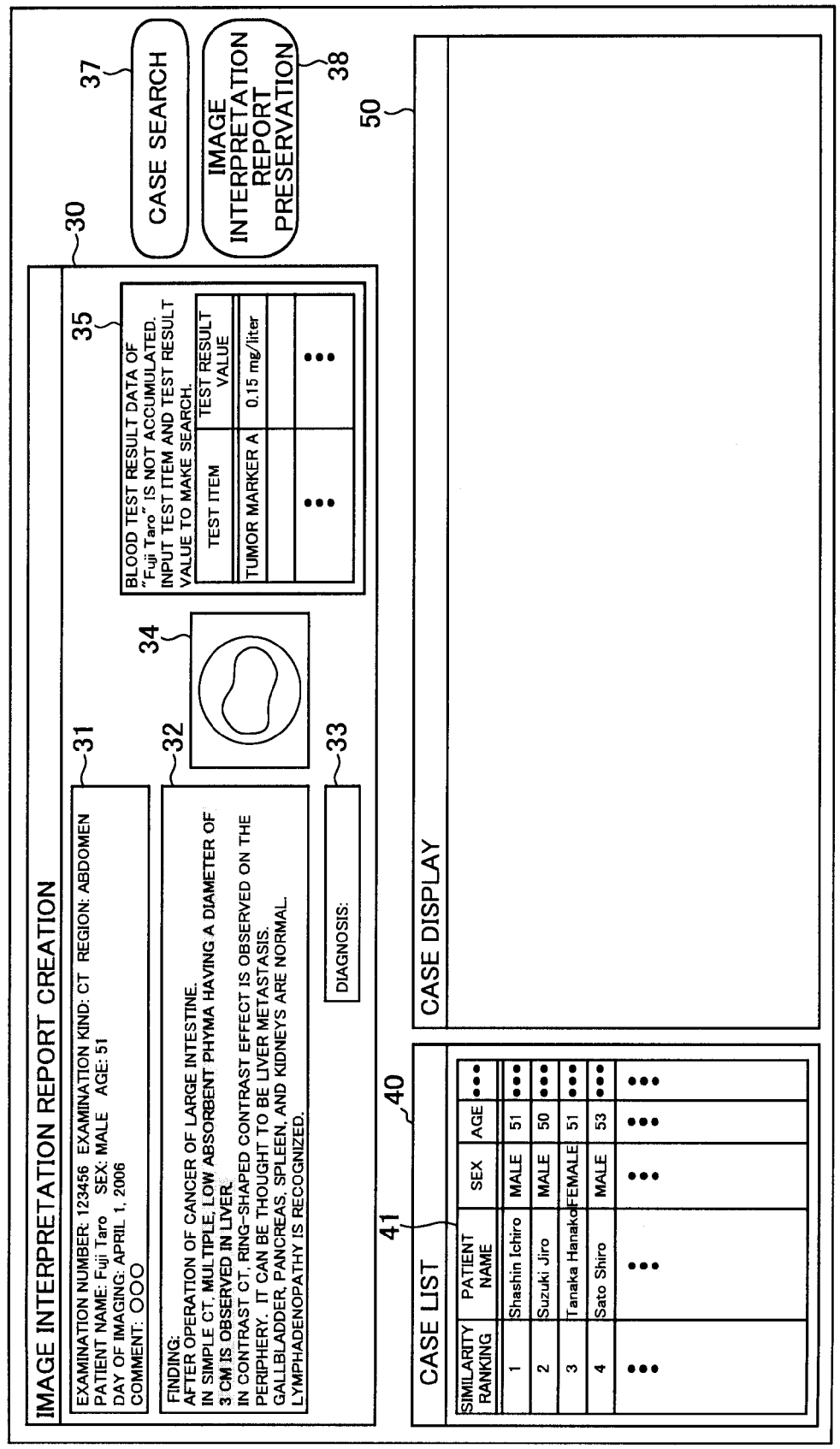
FIG. 23 is a schematic diagram showing an image interpretation report creation screen.

Then, the similarity degree determining unit 20 sorts the combination results of the search result combining unit 19 in the order of the degree of similarity, and displays them in a list in the case list display column 40 in the image interpretation report creation screen (step S38). FIG. 23 is a diagram showing an example of the image interpretation report creation screen at this time. The contents in the case list display column 41 shown in FIG. 23 are the same as those in FIG. 12.

Figure 24:
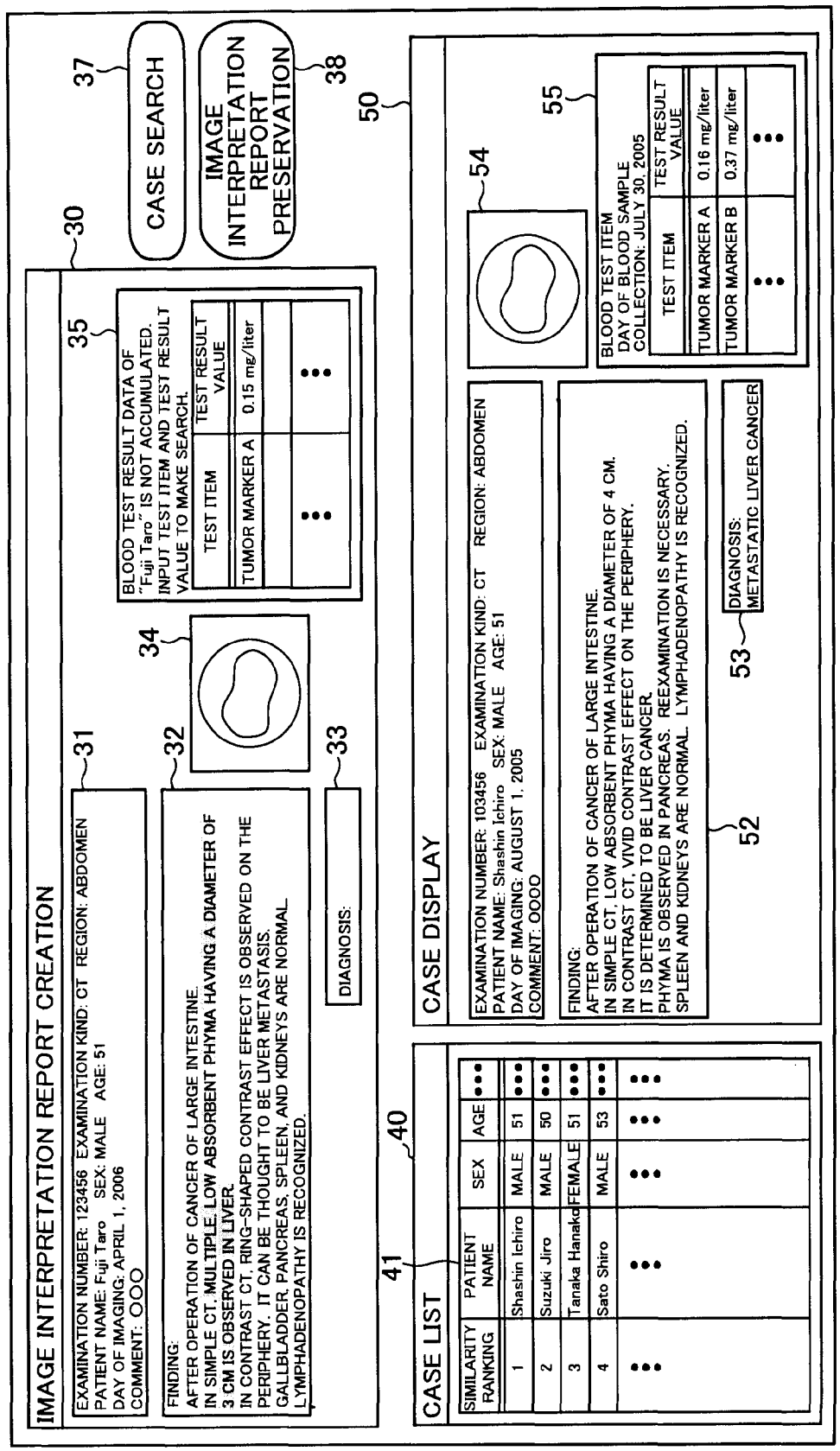
FIG. 24 is a schematic diagram showing an image interpretation report creation screen.

The image interpretation doctor selects a desired case from among the cases displayed in a list in the case list display column 41 by using a mouse. The case display unit 21 displays the contents of the case selected by the image interpretation doctor in the case display column 50 on the display unit 100 (step S39). Here, it is assumed that the image interpretation doctor selects the case of the patient name "Shashin Ichiro". FIG. 24 is a diagram showing an example of the image interpretation report creation screen at this time. By the way, the contents in the case display column 50 shown in FIG. 24 are the same as those in FIG. 15 and FIG. 16.

By the way, the image interpretation doctor can repeat the search for a case until the case that will serve as a reference for a diagnosis of the patient as an object of image interpretation is obtained. This can be realized by the repetition of steps S33 to S38 shown in FIG. 17 by the image interpretation report creating apparatus 1.

In addition, the image interpretation doctor can repeat the selection of a case from among the cases displayed in the list until the case that will serve as a reference for a diagnosis of the patient as an object of image interpretation is obtained. This can be realized by the repetition of step S39 shown in FIG. 17 by the image interpretation report creating apparatus 1.

When the case that will serve as a reference for a diagnosis of the patient as an object of image interpretation is displayed, the image interpretation doctor inputs the diagnostic result in the diagnostic result entry column 33 with reference to the case. Then, when the image interpretation doctor clicks the image interpretation report preservation button 38 (FIG. 24 etc.) in the image interpretation report creation screen, the image interpretation report preservation unit 22 causes the image interpretation report server 4 to store the image interpretation report in the image interpretation report database 4a (step S40).

As described above, according to the image interpretation report creating apparatus of the present embodiment, it is possible to display a case that is a combination of an image interpretation report and a blood test result even if the blood test result data of the patient as an object of image interpretation is not accumulated in the blood test result database 5a. By referring to such a case, the image interpretation doctor can easily make a diagnosis.

By the way, here, the image interpretation doctor inputs a desired blood test item (here, "tumor marker A") and its value (here, "0.15 mg/liter") as shown in FIG. 22, however, the image interpretation doctor may also input a desired blood test item (for example, "tumor marker A") and its value (for example, "0.15 mg/liter to 0.16 mg/liter") as shown in FIG. 25, and the blood test result search processing unit 18 may use the blood test item and its value range ("0.15 mg/liter to 0.16 mg/liter") input by the image interpretation doctor as a search key. Due to this, the image interpretation doctor can acquire a case of a desired blood test result without being restricted by the relation condition setting data (refer to FIG. 4 (*b*)) relating to the blood test result.

The invention claimed is:

1. An image interpretation report creating apparatus to be used for creating an image interpretation report when connected directly or via a network to at least one terminal for displaying a medical image, an image server for storing image data of medical images, an image interpretation report server for storing image interpretation report database accumulating image interpretation report data of image interpretation reports created based on medical images, and at least one examination result server for storing examination result database accumulating examination result data of examination results obtained by examination using no medical image, said apparatus comprising:

a display unit for displaying an image interpretation report creation screen for creating an image interpretation report of a medical image obtained by examination using a medical image along with an examination result obtained by examination using no medical image;

input means to be used for inputting finding of the medical image and specifying first information and second information in the finding and an examination result displayed on said display unit, respectively;

search key generating means for generating at least one first search key for searching said image interpretation report database and at least one second search key for searching said examination result database, based on the first and second information, respectively;

search processing means for causing said image interpretation report server to obtain at least one case that matches said at least one first search key and causing said examination result server to obtain at least one case that matches said at least one second search key;

similarity degree determining means for determining a degree of similarity between (i) the first and second information specified in the finding and the examination result displayed on said display unit and (ii) the at least one case obtained by said image interpretation report server and said examination result server, and displaying the obtained at least one case in a list on said display unit in an order of the degree of similarity;

case display means for displaying contents of a case, which is selected by a user from among the at least one case displayed in the list, on said display unit; and image interpretation report preservation means for causing said image interpretation report server to store image interpretation report data of the image interpretation report created based on the image interpretation report creation screen displayed on said display unit.

2. The image interpretation report creating apparatus according to claim 1, wherein said search processing means includes:

image interpretation report search processing means for causing said image interpretation report server to search said image interpretation report database for image interpretation report data representing a case that matches said at least one first search key to obtain the image interpretation report data, and outputting the obtained image interpretation report data; and examination result search processing means for adding condition about examination information included in the image interpretation report data obtained by said image interpretation report search processing means to said at least one second search key to obtain a combined search key, and causing said examination result server to search said examination result server database for examination result data representing a case that matches the combined search key to obtain the examination result data, and outputting the obtained examination result data.

3. The image interpretation report creating apparatus according to claim 2, further comprising:

storage means for storing data of relationship that should be met between the examination using the medical image and the examination using no medical image;

wherein said examination result search processing means adds condition about the relationship, that should be met for the examination information included in the image interpretation report data obtained by said image interpretation report search processing means, to said at least one second search key, based on the relationship represented by the data stored in said storage means.

4. The image interpretation report creating apparatus according to claim 1, wherein said similarity degree determining means determines a comprehensive degree of similarity based on (i) a first degree of similarity between the first information specified in the finding displayed on said display unit and said at least one case obtained by said image interpretation report server and (ii) a second degree of similarity between the second information specified in the examination result displayed on said display unit and said at least one case obtained by said examination result server.

5. The image interpretation report creating apparatus according to claim 1, wherein, when the examination result of a patient as an object of image interpretation is not accumulated in said examination result database, said input means is used to input third information for searching said examination result database for at least one case, and said search key generating means generates said at least one first search key and said at least one second search key based on said first and third information, respectively.

6. The image interpretation report creating apparatus according to claim 5, wherein said similarity degree determining means determines a comprehensive degree of similarity based on (i) a first degree of similarity between the first information and said at least one case obtained by said image interpretation report server and (ii) a second degree of similarity between the third information and said at least one case obtained by said examination result server.

7. The image interpretation report creating apparatus according to claim 1, wherein, when examination result of a patient as an object of image interpretation is not accumulated in said examination result database, said input means is used to input at least one third search key for searching said examination result database for at least one case, said search key generating means generates at least one first search key for searching said image interpretation report database for at least one case based on the first information, said search processing means causes said image interpretation report server to obtain at least one case that matches said at least one first search key and causes said examination result server to obtain at least one case that matches said at least one third search key, and said similarity degree determining means determines a degree of similarity between the first information specified in the finding displayed on said display unit and each of the cases obtained by said image interpretation report server, and displays the obtained cases in a list on said display unit in an order of the degree of similarity.

* * * * *